(12) United States Patent
Nerurkar et al.

(10) Patent No.: US 8,999,952 B2
(45) Date of Patent: *Apr. 7, 2015

(54) ARIPIPRAZOLE COMPLEX FORMULATION AND METHOD

(71) Applicant: Otsuka Pharmaceutical Co., Ltd., Tokyo (JP)

(72) Inventors: Manoj Nerurkar, Bangalore (IN); Vijay H. Naringrekar, Princeton, NJ (US)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/872,517

(22) Filed: Apr. 29, 2013

(65) Prior Publication Data

US 2014/0235574 A1 Aug. 21, 2014

Related U.S. Application Data

(63) Continuation of application No. 13/656,785, filed on Oct. 22, 2012, now abandoned, which is a continuation of application No. 13/288,077, filed on Nov. 3, 2011, now abandoned, which is a continuation of application No. 13/046,124, filed on Mar. 11, 2011, now abandoned, which is a continuation of application No. 12/417,067, filed on Apr. 2, 2009, now abandoned, which is a continuation of application No. 11/452,782, filed on Jun. 14, 2006, now Pat. No. 7,550,445, which is a continuation of application No. 10/642,366, filed on Aug. 14, 2003, now Pat. No. 7,115,587.

(60) Provisional application No. 60/404,713, filed on Aug. 20, 2002.

(51) Int. Cl.

| A61K 47/40 | (2006.01) |
|---|---|
| A61K 47/48 | (2006.01) |
| A61K 31/496 | (2006.01) |
| A61K 9/00 | (2006.01) |
| A61K 47/12 | (2006.01) |
| B82Y 5/00 | (2011.01) |
| A61P 25/18 | (2006.01) |

(52) U.S. Cl.
CPC ........... *A61K 47/4823* (2013.01); *A61K 9/0019* (2013.01); *A61K 31/496* (2013.01); *A61K 47/12* (2013.01); *A61K 47/48969* (2013.01); *B82Y 5/00* (2013.01)

(58) Field of Classification Search
None
See application file for complete search history.

(56) References Cited

U.S. PATENT DOCUMENTS

| 4,983,586 A | 1/1991 | Bodor |
|---|---|---|
| 5,006,528 A | 4/1991 | Oshiro et al. |
| 5,134,127 A | 7/1992 | Stella et al. |
| 5,376,645 A | 12/1994 | Stella et al. |
| 5,646,131 A | 7/1997 | Badwan et al. |
| 5,773,029 A | 6/1998 | Chiesi et al. |
| 5,855,916 A | 1/1999 | Chiesi et al. |
| 5,904,929 A | 5/1999 | Uekama et al. |
| 6,232,304 B1 | 5/2001 | Kim et al. |
| 6,407,079 B1 | 6/2002 | Müller et al. |
| 6,632,803 B1 | 10/2003 | Harding |
| 6,713,461 B1 | 3/2004 | Billotte |
| 6,977,257 B2 | 12/2005 | Parab et al. |
| 7,115,587 B2 | 10/2006 | Nerurkar et al. |
| 7,550,445 B2 | 6/2009 | Nerurkar et al. |
| 2004/0146562 A1 | 7/2004 | Shah |

FOREIGN PATENT DOCUMENTS

| EP | 1145711 | 10/2001 |
|---|---|---|
| JP | 9-301867 | 11/1997 |
| WO | WO 03/026659 A1 | 4/2003 |
| WO | WO 03/064393 A1 | 8/2003 |

OTHER PUBLICATIONS

Szejtli, J., "Cyclodextrins in Drug Formulations: Part I", Pharmaceutical Technology International, vol. 3, No. 2, pp. 15-22, 1991.
Szejtli, J., "Cyclodextrins in Drug Formulations: Part II", Pharmaceutical Technology International, vol. 3, No. 3, pp. 16-24, 1991.
Rajewski, R.A., et al., "Pharmaceutical Applications of Cyclodextrins. 2. In Vivo Drug Delivery", Journal of Pharmaceutical Sciences, vol. 85, No. 11, 1996, pp. 1142-1169.

*Primary Examiner* — Leigh Maier
(74) *Attorney, Agent, or Firm* — Finnegan, Henderson, Farabow, Garrett & Dunner, LLP

(57) ABSTRACT

An aripiprazole formulation is provided which includes the antipsychotic agent aripiprazole in the form of an inclusion complex in a β-cyclodextrin, preferably, sulfobutyl ether β-cyclodextrin (SBECD), which in the form of an injectable produces reversible generally minimal to mild irritation at the intramuscular injection site. A method for minimizing or reducing irritation caused by aripiprazole at an intramuscular injection site and a method for treating schizophrenia employing the above formulation are also provided.

6 Claims, No Drawings

ARIPIPRAZOLE COMPLEX FORMULATION AND METHOD

CROSS REFERENCE TO RELATED APPLICATION

This Continuation application claims the benefit of U.S. Ser. No. 13/656,785 filed Oct. 22, 2012, now pending, which is a Continuation application which claims the benefit of U.S. Ser. No. 13/288,077 filed Nov. 3, 2011, now abandoned, which is a Continuation application which claims the benefit of U.S. Ser. No. 13/046,124 filed Mar. 11, 2011, now abandoned, which is a Continuation application which claims the benefit of U.S. Ser. No. 12/417,067 filed Apr. 2, 2009, now abandoned, which is a Continuation application which claims the benefit of U.S. Ser. No. 11/452,782 filed Jun. 14, 2006, now U.S. Pat. No. 7,550,445, which is a Continuation application which claims the benefit of U.S. Ser. No. 10/642,366 filed Aug. 14, 2003, now U.S. Pat. No. 7,115,587, which claims the benefit of U.S. Provisional Application Ser. No. 60/404,713 filed Aug. 20, 2002.

FIELD OF THE INVENTION

The present invention relates to an aripiprazole inclusion complex with a substituted-β-cyclodextrin, an aripiprazole formulation which includes aripiprazole in the form of the above inclusion complex, an injectable formulation which contains the above complex of aripiprazole, a method for reducing irritation normally caused by aripiprazole at an intramuscular injection site employing the above injectable formulation and a method for treating schizophrenia employing the above formulation.

BACKGROUND OF THE INVENTION

U.S. Pat. No. 5,006,528 to Oshiro et al. discloses 7-[(4-phenylpiperazino)-butoxy]carbostyrils, which include aripiprazole, as dopaminergic neurotransmitter antagonists.

Aripiprazole which has the structure

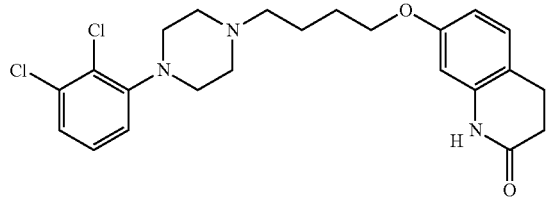

is an atypical antipsychotic agent useful in treating schizophrenia. It has poor aqueous solubility (<1 μg/mL at room temperature). When formulated as an intramuscular (IM) injectable solution, aripiprazole has been found to cause unacceptable (moderate to severe) tissue irritation at the muscular site with many water-miscible co-solvent systems, and water-immiscible solvent and co-solvent systems such as hexonoic acid: medium chain triglyceride (10:90), polyethylene glycol 400:ethanol:lactic acid (35:15:50), benzyl alcohol:sesame oil (10:90), benzyl alcohol:medium chain triglyceride (10:90), benzyl alcohol:tributyrin (5:95), and polysorbate 80 in 25 mM tartaric acid.

Cyclodextrins are known for their use in increasing solubility of drugs. They function by forming inclusion complexes with hydrophobic molecules. Unfortunately, there are many drugs for which cyclodextrin complexation either is not possible or produces no apparent advantages as disclosed by J. Szejtli, *Cyclodextrins in Drug Formulations: Part II, Pharmaceutical Technology*, 24-38, August, 1991.

U.S. Pat. Nos. 5,134,127 and 5,376,645 each to Stella et al. disclose sulfoalkyl ether cyclodextrin derivatives and their use as solubilizing agents for water-insoluble drugs for oral, intranasal or parenteral administration including intravenous and intramuscular. Stella et al. disclose an inclusion complex of the water-insoluble drug and the sulfoalkyl ether cyclodextrin derivative and pharmaceutical compositions containing same. Examples of sulfoalkyl ether cyclodextrin derivatives disclosed include mono-sulfobutyl ether of β-cyclodextrin and monosulfopropyl ether of β-cyclodextrin. Examples of water-insoluble drugs are set out in column 7 starting at line 25 and include, among others, benzodiazepines, chlorpromazine, diazepam, mephorbarbital, methbarbital, nitrazepam, and phenobarbital.

U.S. Pat. No. 6,232,304 to Kim et al. discloses inclusion complexes of arylheterocyclic salts such as the tartrate salt of ziprasidone in a cyclodextrin such as β-cyclodextrin sulfobutyl ether (SBECD), and hydroxypropyl-β-cyclodextrin (HP-BCD), and use of such inclusion complexes in oral and parenteral formulations.

Japanese Patent Application No. 09301867A2 dated Nov. 25, 1997 discloses antidepressant compositions in the form of tablets containing aripiprazole.

EP1145711A1 dated Oct. 17, 2001 (based on U.S. Application Serial No. 2000-547948 filed Apr. 12, 2000) discloses flash-melt oral dosage formulations containing aripiprazole.

U.S. Pat. No. 5,904,929 to Uekama et al. discloses transmucosal and transdermal pharmaceutical compositions containing a drug and a peracylated cyclodextrin as a solubilizing agent. Examples of drugs include antidepressants such as amitriptyline HCl, amoxapine, butriptyline HCl, clomipramine HCl, desipramine HCl, dothiepin HCl, doxepin HCl, fluoxetine, gepirone, imipramine, lithium carbonate, mianserin HCl, milnacipran, nortriptyline HCl and paroxetine HCl; anti-muscarinic agents such as atropine sulphate and hyoscine; sedating agents such as alprazolam, buspirone HCl, chlordiazepoxide HCl, chlorpromazine, clozapine, diazepam, flupenthixol HCl, fluphenazine, flurazepam, lorazepam, mazapertine, olanzapine, oxazepam, pimozide, pipamperone, piracetam, promazine, risperidone, selfotel, seroquel, sulpiride, temazepam, thiothixene, triazolam, trifluperidol and ziprasidone; anti-migraine drugs such as alniditan and sumatriptan; beta-adrenoreptor blocking agents such as atenolol, carvedilol, metoprolol, nebivolol and propranolol; anti-Parkinsonian drugs such as bromocryptine mesylate, levodopa and selegiline HCl; opioid analgesics such as buprenorphine HCl, codeine, dextromoramide and dihydrocodeine; parasympathomimetics such as galanthamine, neostigmine, physostymine, tacrine, donepezil, ENA 713 (exelon) and xanomeline; and vasodilators such as amlodipine, buflomedil, amyl nitrite, diltiazem, dipyridamole, glyceryl trinitrate, isosorbide dinitrate, lidoflazine, molsidomine, nicardipine, nifedipine, oxpentifylline and pentaerythritol tetranitrate.

BRIEF DESCRIPTION OF THE INVENTION

In accordance with the present invention, there is provided an inclusion complex of aripiprazole in a substituted-beta-cyclodextrin. It has been found that the inclusion complex of aripiprazole is substantially more water-soluble relative to the non-complexed aripiprazole.

Surprisingly and unexpectedly, it has been found that when aripiprazole is complexed with a substituted β-cyclodextrin such as sulfobutyl ether-β-cyclodextrin, it may be formulated as an injectable which delivers aripiprazole to the muscular site with unexpectedly diminished irritation as compared to injectables containing uncomplexed aripiprazole.

In addition, in accordance with the present invention, a pharmaceutical formulation is provided which is formed of an inclusion complex of aripiprazole and a substituted-β-cyclodextrin, and a pharmaceutically acceptable carrier therefor.

In a preferred embodiment, the pharmaceutical formulation of the invention will be in the form of an aqueous parenteral or injectable formulation. However, the pharmaceutical formulation of the invention may be in other dosage forms such as lyophilized injectable, oral (for example tablets, capsules, elixirs and the like), transdermal or transmucosal forms or inhalation forms.

Further, in accordance with the present invention, a method is provided for administering injectable aripiprazole without causing unacceptable irritation at the site of injection wherein the above described injectable formulation is administered, preferably intramuscularly, to a patient in need of treatment.

Still further in accordance with the present invention, a method is provided for treating schizophrenia which includes the step of administering to a patient in need of treatment the above described formulation, preferably in injectable form, without causing undue irritation at the site of injection, whether it be at a muscular site or other site.

DETAILED DESCRIPTION OF THE INVENTION

Aripiprazole has poor water solubility and thus is difficult to formulate as an aqueous injectable. In accordance with the present invention, it as been found that the water-solubility of aripiprazole may be sufficiently increased to allow it to be formulated as an aqueous injectable by complexing aripiprazole with a substituted-β-cyclodextrin. In effect, the cyclodextrin inhibits precipitation of the aripiprazole at the site of injection. The aqueous injectable formulation containing the complex of aripiprazole and the substituted-β-cyclodextrin may be administered preferably intramuscularly without causing unacceptable irritation at the muscular site. This is indeed surprising and unexpected since, as indicated above, a host of water-miscible co-solvent systems and water-immiscible co-solvent systems have been found to be unacceptable as carriers for injectable aripiprazole formulations because of the unacceptable irritation profile of such formulations. On the other hand, the aqueous injectable formulation of the invention delivers aripiprazole without causing unacceptable irritation at the site of injection.

As will be seen hereinafter, the aripiprazole formulation in the form of an aqueous injectable will include an acid buffer and a base to adjust pH to desired levels.

The substituted-β-cyclodextrin suitable for use herein refers to sulfobutyl ether β-cyclodextrin (SBECD) and hydroxypropyl-β-cyclodextrin (HPBCD), with SBECD being preferred.

The term "undue irritation" or "unacceptable irritation" at the site of injection or at the muscular site refers to moderate to severe irritation which is unacceptable to the patient and thereby impacts unfavorably on patient compliance.

The term "reduced irritation" at the site of injection or at the muscular site refers to generally minimal to mild irritation which is acceptable to the patient and does not impact unfavorably on patient compliance.

The aripiprazole will form a complex with the substituted-β-cyclodextrin which complex may be dissolved in water to form an injectable formulation. However, physical mixtures of aripiprazole and the substituted-β-cyclodextrin are within the scope of the present invention as well.

The complex or the physical mixture may also be compressed into a tablet or may be filled into capsules.

The aripiprazole formulations of the invention may be formed of dry physical mixtures of aripiprazole and the substituted-β-cyclodextrin or dry inclusion complexes thereof which upon addition of water are reconstituted to form an aqueous injectable formulation. Alternatively, the aqueous injectable formulation may be freeze dried and later reconstituted with water. Thus, the inclusion complex in accordance with the invention, may be pre-formed, formed in situ or formed in vivo (in the gastrointestional tract or the buccal cavity). All of the above are contemplated by the present invention.

The aripiprazole formulation of the invention in the form of an aqueous injectable will include an acid buffer to adjust pH of the aqueous injection within the range from about 3.5 to about 5. Examples of acid buffers suitable for use herein include acids such as hydrochloric acid, sulfuric acid, phosphoric acid, hydrobromic acid and the like, and organic acids such as oxalic acid, maleic acid, fumaric acid, lactic acid, malic acid, tartaric acid, citric acid, benzoic acid, acetic acid, methanesulfonic acid, toluenesulfonic acid, benzenesulfonic acid, ethanesulfonic acid and the like. Acid salts of the above acids may be employed as well. Preferred acids are tartaric acid, citric acid, and hydrochloric acid. Most preferred is tartaric acid.

The injectable formulation of the invention will have a pH within the range from about 3.5 to about 5, preferably from about 4 to about 4.6, and most preferably about 4.3. In formulating the injectable, if necessary, the pH may be adjusted with a base such as an alkali metal hydroxide such as NaOH, KOH, or LiOH, preferably NaOH, or an alkaline earth metal hydroxide, such as $Mg(OH)_2$ or $Ca(OH)_2$.

In preparing the aqueous injectable formulation of the invention, the substituted-β-cyclodextrin will be employed in a weight ratio to the aripiprazole within the range from about 5:1 to 400:1, preferably from about 10:1 to about 100:1. Each type of cyclodextrin employed requires a different ratio to inhibit or prevent precipitation of aripiprazole at the injection site. In preferred embodiments of the aqueous injectable of the invention, the substituted-β-cyclodextrin will be SBECD which will be employed in a weight ratio to aripiprazole within the range from about 5:1 to about 400:1, preferably from about 20:1 to about 40:1. The cyclodextrin may be present in an amount greater than that needed to complex the aripiprazole since the additional cyclodextrin could aid in dissolution of the aripiprazole.

The aripiprazole will be present in the aqueous injectable formulation in an amount within the range from about 0.1 to about 2.5% by weight, preferably from about 0.2 to about 1.5% by weight based on the total injectable formulation.

In preferred embodiments, the aripiprazole will be present in the aqueous injectable formulation to provide from about 1 to about 20 mg/mL of formulation, preferably from about 1.5 to about 8 mg/mL of formulation.

In more preferred embodiments, the formulations of the invention will provide 2 mg aripiprazole/mL, 5 mg/mL and 7.5 mg/mL. Fill volumes will preferably be 0.5 mL and 2 mL.

A preferred injectable formulation is as follows:
(1) aripiprazole—in an amount to provide from about 1.5 to about 8 mg/mL of solution.
(2) SBECD—in an amount from about 100 to about 200 mg/mL of solution.

(3) acid buffer (preferably tartaric acid)—in an amount from about 7 to about 9 mg/mL of solution to adjust pH from about 3.5 to about 5.
(4) base to adjust pH, preferably an alkali metal hydroxide, preferably NaOH—in an amount to adjust pH from about 4 to 4.6
(5) water qs to 1 mL.

The aripiprazole injectable formulation of the invention may be prepared as follows: Tartaric acid or other acid buffer is dissolved in water for injection. The substituted-β-cyclodextrin (preferably SBECD) is dissolved in the acid buffer-water solution. Aripiprazole is then dissolved in the solution. The pH of the solution is adjusted to within the range from about 3.5 to about 5, preferably about 4.3 by adding base, such as sodium hydroxide or other alkali metal hydroxide or alkaline earth metal hydroxide. Additional water for injection is added to obtain the desired batch volume.

The resulting solution is aseptically filtered, for example, through a 0.22μ membrane filter and filled into vials. The vials are stopped and sealed and terminally sterilized.

The aqueous injectable formulation of the invention will provide an amount of aripiprazole of at least 2 mg aripiprazole/mL, preferably at least 5 mg aripiprazole/mL, when the amount of aripiprazole provided by the complex is measured at a cyclodextrin concentration of 5% w/v in water.

The aripiprazole formulations of the invention are used to treat schizophrenia in human patients. The preferred dosage employed for the injectable formulations of the invention will be a 2 ml injection containing 7.5 mg aripiprazole/mL or a dose of 15 mg given three times daily at two hour intervals. The injectable formulation is preferably administered intramuscularly although subcutaneous and intravenous injections are effective as well.

The following example represents a preferred embodiment of the invention.

EXAMPLE

A clear colorless aripiprazole injectable solution (2 mg aripiprazole/mL, 4 mg/vial) essentially free of particulate matter by visual inspection was prepared as follows.

A stainless steel batching vessel was charged with an appropriate amount of water for injection USP.

With continuous stirring, 78 g tartaric acid granular USP and 1500 g sulfobutyl ether β-cyclodextrin (SBECD) was added to the batching vessel and was dissolved in the water.

Aripiprazole 20 g was added to the batching vessel and stirring was continued until the aripiprazole was dissolved.

Sodium hydroxide 1N was added to the above solution to adjust the pH thereof to about 4.3.

Additional water for injection USP was added to the above solution to adjust to the final batch size to 10 L with stirring.

The above solution was aseptically filtered through a 0.22 μM membrane filter into a sterilized container 4 mg amounts of the above solution were aseptically filled into sterilized vials which were then aseptically stoppered with sterilized stoppers to seal the vials.

What is claimed is:

1. An aqueous injectable formulation having a pH of from about 3.5 to about 5, comprising:
    a) a complex comprising aripiprazole and sulfobutyl ether-β-cyclodextrin;
    b) tartaric acid;
    c) sodium hydroxide; and
    d) wafer for injection.

2. The formulation as defined in claim 1 which contains 2 mg aripiprazole/ml, 5 mg aripiprazole/ml or 7.5 mg aripiprazole/ml.

3. The formulation as defined in claim 1 comprising from about 0.1 to about 2.5% by weight aripiprazole.

4. The formulation as defined in claim 1 comprising from about 0.2 to about 1.5% by weight aripiprazole.

5. The formulation as defined in claim 1 wherein the sulfobutyl ether-β-cyclodextrin is present in an amount from about 100 to about 700 mg/m of solution.

6. The formulation as defined in claim 1 wherein the tartaric acid is present in an amount from about 7 to about 9 mg/mi.

* * * * *